United States Patent [19]

Iwasaki et al.

[11] Patent Number: 5,091,312
[45] Date of Patent: Feb. 25, 1992

[54] PROCESS FOR THE PREPARATION OF SARCOSINE OXIDASE

[75] Inventors: Hiroya Iwasaki; Katsuyuki Fujimura, both of Hyogo; Yoshio Inoue; Shoshiro Nakamura, both of Hiroshima, all of Japan

[73] Assignee: Kobayashi Pharmaceutical Co., Ltd., Osaka, Japan

[21] Appl. No.: 598,828

[22] Filed: Oct. 16, 1990

Related U.S. Application Data

[63] Continuation of Ser. No. 158,408, Feb. 22, 1988, abandoned.

[30] Foreign Application Priority Data

Feb. 27, 1987 [JP] Japan .................................. 62-46494

[51] Int. Cl.$^5$ .............................................. C12N 9/06
[52] U.S. Cl. .................................... 435/191; 435/106; 435/147
[58] Field of Search ........................ 435/191, 106, 147

[56] References Cited

U.S. PATENT DOCUMENTS 4,743,549  5/1988  Mayr et al. .......................... 435/191

Primary Examiner—Charles L. Patterson
Attorney, Agent, or Firm—Koda and Androlia

[57] ABSTRACT

This invention relates to a process of producing sarcosine oxidase by cultivating microorganisms belonging to genus Streptomyces and possessing an ability to produce sarcosine oxidase, and collecting sarcosine oxidase from the obtained culture. As an example of said microorganisms used in this invention, *Streptomyces sp.* KB210-8SY discovered by the prevent inventor is known.

Said microorganisms are cultivated usually by using a culture medium, and from the obtained culture, sarcosine oxidase is isolated and purified.

2 Claims, 3 Drawing Sheets

○ : Phosphate buffer (pH 6.0~7.5)

● : Tris-HCl buffer (pH 7.5~9.0)

△ : Carbonate buffer (pH 9.0~10.0)

Thermal stability

PROCESS FOR THE PREPARATION OF SARCOSINE OXIDASE

This is a continuation of application Ser. No. 158,408, filed Feb. 22, 1988 now abandoned.

BACKGROUND OF THE INVENTION

1. Field of the Invention

This invention relates to a process of preparation of sarcosine oxidase, and more particularly to a method of producing sarcosine oxidase by incubating microorganisms belonging to genus Streptomyces and possessing sarcosine oxidase producing ability.

2. Prior Art

In the field of clinical medicine, creatinine and creatine in serum or urine are determined for diagnosis of renal function disorders or muscular diseases. Recently, as the method of this assay, methods to determine creatinine and creatine enzymatically are reported as the process depending on the following reactions (a) to (c) (formaldehyde or hydrogen peroxide in the reaction product is determined by a known method), and sarcosine oxidase (E.C.1.5.3.1) is used in such methods.

(Creatinine amidohydrolase)

(a) Creatinine + $H_2O$ ⇌ Creatine (Creatine amidinohydrolase)

(b) Creatine + $H_2O$ → Sarcosine + urea (Sarcosine Oxidase)

(c) Sarcosine + $O_2$ + $H_2O$ → Glycine + formaldehyde + $H_2O_2$

Sarcosine oxidase is, as indicated in reaction formula (c), a enzyme which catalyzes the reaction to produce glycine, formaldehyde and hydrogen peroxide by acting on sarcosine. Sarcosine oxidase has been conventionally known, and is known to be present in the microorganisms belonging to the species of Corynebacterium, Arthrobacter, Bacillus, Cylindrocarbon and Pseudomonas.

However, to obtain sarcosine oxidase existing in the above microorganisms, it is necessary to collect culture cells, triturate them, and treat ultrasonically or bacteriolytically to isolate sarcosine oxidase and extract, and the purifying operation is extremely complicated, and sarcosine oxidase cannot be obtained easily and efficiently.

BRIEF SUMMARY OF THE INVENTION

This invention is devised in the light of the above-mentioned background, and is intended to present a process of obtaining sarcosine oxidase easily and efficiently.

It is another object of this invention to present a preparing method of sarcosine oxidase which is extremely easy in the purifying operation of sarcosine oxidase.

In order to achieve those and other objects, this invention is characterized by incubation of microorganisms belonging to genus Streptomyces and possessing sarcosine oxidase producing ability, and collecting sarcosine oxidase from the obtained culture.

The microorganisms used in this invention are not particularly limited as far as they belong to genus Streptomyces and possess the ability to produce sarcosine oxidase.

As a practical example of microorganism used in this invention, below are described taxonomical properties of KB210-8SY strain which the present inventor collected from the soil in the town of Nachi Katsuura, Higashimuro-gun, Wakayama Prefecture.

A) Microscopic Observation

After cultivation on starch, inorganic salt agar culture medium at 27° C., for 10 to 14 days, the following morphological findings were obtained by microscopic observation.

The aerial mycelium had a moderate flexuous shape with a simple branching. The matured spore chain contained 10 to 50 spores in a linked chain. The spores were somewhat ellipsoid, and measured 0.6 to 0.7 μm by 0.6 to 0.8 μm, and the spore surface was smooth.

B) Macroscopic Observations

The results of macroscopic observation of growth on various culture media (27° C., 14-day cultivation) are as shown in Table 1.

In this table, description of colors conforms to the *Color Harmony Manual*, 4th edition, 1958 (Container Corporation of America).

TABLE 1

| Culture medium | Growth | Color of substrate mycelium | Aerial mycelium | Soluble Pigment |
|---|---|---|---|---|
| Sucrose-nitrate agar medium | Poor | Covert tan (2ge) | Poor: adobe brown (3lg) | None |
| Glucose-asparagine agar medium | Moderate | Light ivory (2ca) | Poor or moderate: white (a) or natural (3dc) | None |
| Glycerin-asparagine agar medium | Good | Covert tan (2ge) | Good: white (a) or silver gray (3fe) | None |
| Starch-inorganic salt agar medium | Good | Yellowish brown (2gn) | Good: silver gray (3fe) or natural (3dc) | None |
| Tyrosine agar medium | Moderate | Light mustard tan (2is) | Good: silver gray (3fe) or white (a) | None |
| Nutrient agar medium | Moderate | Light ivory (2ca) | Poor: white (a) | None |
| Yeast extract-malt extract agar medium | Good | Bamboo (2gc) | Abundant: white (a) or gray (g) | None |
| Oatmeal agar medium | Good | Bamboo (2gc) | Poor: camel (3ig) | None |

C) Physiological Properties

1. Growth temperature range 20° to 43° C. Optimum temperature is around 35° C.

2. Liquefaction of gelatin (glucose-peptone-gelatin medium, 27° C. cultivation): Negative.

3. Hydrolysis of starch (starch-inorganic salt agar medium, 27° C. cultivation): Positive.

4. Coagulation, peptonization of skim milk (skim milk, 37° C. cultivation) Coagulation: Negative, Peptonization: Positive.

5. Melanin pigment production Tyrosine agar medium (27° C. cultivation): Negative. Peptone-yeast extract-iron agar medium (27° C. cultivation): Negative. Tryptone-yeast extract broth (27° C. cultivation): Negative.

D) Utilization of Carbon Sources

Utilization of various carbon sources on Pridham and Gottlieb carbon utilization medium is as shown in Table 2.

TABLE 2

| Carbon source | Utilization |
| --- | --- |
| L-Arabinose | Negative |
| D-Xylose | Positive |
| D-Glucose | Positive |
| D-Fructose | Positive |
| Sucrose | Doubtful |
| Inositol | Negative |
| L-Rhamnose | Negative |
| Raffinose | Positive |
| D-Mannitol | Positive |

E) Composition of Diaminopimelic Acid

In analysis of the whole cell, L-diaminopimelic acid was detected, but meso-type was not detected.

Based on the above properties, when this strain was compared with the classification by *Bergey's Manual of Determinative Bacteriology*, 8th edition, 1974, it was confirmed to belong to genus Streptomyces, and was hence named as Streptomyces sp. KB210-8SY. Meanwhile, this strain is deposited to Fermentation Research Institute of Agency of Industrial Science and Technology of the Ministry of International Trade and Industry of Japan. (Date deposited: Feb. 17, 1987; entrustment No.: FERM BP-1292; deposited organ: Fermentation Research Institute, Agency of Industrial Science and Technology, Ministry of International Trade and Industry, 1-3 Higashi 1-chome, Yatabe-machi, Tsukuba-gun, Ibaraki-ken 305, Japan; classification: actinomycete)

Described below is the method of producing sarcosine oxidase of this invention by using the above strain.

The preparing process of this invention fundamentally lies in the use of biosynthesizing function of enzyme protein by the gene deoxyribonucleic acid (DNA) responsible for genetic information relating to production of sarosine oxidase by the microorganism belonging to genus Streptomyces.

The microorganisms belonging to genus Streptomyces used in this invention may be cultivated either in solid culture medium or liquid culture medium, but it is preferable to operate shaking culture or aeration-agitation submerged culture by using liquid culture medium.

As the nutrient source of the culture medium, those used in cultivation of microorganisms may be widely used. As the nitrogen source, any usable nitrogen source may be used, and corn steep liquor, soy bean flour, various meat extracts, peptone, yeast extract, ammonium sulfate and ammonium chloride may be used, for example. As the carbon source, any usable carbon compound may be used, and glucose, xylose, soluble starch, glycerin and malt extract may be used, for example. Besides, sodium chloride, potassium chloride, magnesium sulfate, potassium dihydrogen phosphate, dipotassium hydrogen phosphate, calcium carbonate, and various inorganic salts and antifoaming agents are used as required. Or when a choline derivative is added to the culture medium, the accumulation of sarcosine oxidase is increased. As the choline derivative, for example, choline chloride, choline bitartrate may be used. The concentration of its addition is preferably about 0.1% to 1.5%.

The cultivation temperature may be free within the range suited to growth of organism and production of sarcosine oxidase, and is usually 20° to 37° C. The cultivation time varies somewhat depending on the condition, but it is usually 48 to 120 hours, and the cultivation may be properly terminated when the sarcosine oxidase production reaches the maximum.

In thus obtained culture, sarcosine oxidase is mainly obtained from outside the cell. For purification of sarcosine oxidase from the culture, cells and other solid matter are removed by filtration or centrifugation, and the obtained broth containing crude sarcosine oxidase is purified by conventional isolation and purification method for protein and enzyme, so that a purified sarcosine oxidase is obtained. For example, an organic solvent such as acetone, ethanol and methanol is added to the crude sarcosine oxidase to precipitate to separate, or it is precipitated by salting-out method using ammonium sulfate or the like, and the precipitate is collected. To purify this precipitate for example, the precipitate is dissolved in a solvent such as phosphate buffer, tris-HCl buffer and carbonate buffer, and is chromatographed using anion exchanger such as diethylaminoethyl cellulose ion exchanger and diethylaminoethyl dextran ion exchanger, or gel filteration agent such as dextran gel or polyacrylamide gel, or by adsorption-elution method using hydroxyapatite, or by electrophoresis using polyacrylamide gel or the like. These means may be properly selected or combined, and finally by drying by lyophilization or other means, purified sarcosine oxidase powder is obtained.

The enzyme assay and physicochemical properties of the sarcosine oxidase obtained by this invention are described hereinafter.

ENZYME ASSAY

To 0.5 ml of reaction solution composed of 0.05 ml of 0.2M tris-HCl buffer (pH 8.0), 0.05 ml of 15 mM 4-aminoantipyrin aqueous solution, 0.05 ml of 0.2% (w/v) phenol aqueous solution, 0.05 ml of 50 U/ml peroxidase solution, 0.1 ml of 1M sarcosine aqueous solution, and 0.2 ml of distilled water, 10 μl of properly diluted enzyme solution is added, and after allowing to react for 5 minutes at 37° C., ethanol is added to terminate the reaction. Using the specimen at 0 minute of enzyme reaction as the control, the absorbance (ΔA) is measured by spectrophotometer at 480 nm, and the enzyme activity is calculated as follows.

Enzyme activity unit per 1 ml of enzyme solution (U/ml)=ΔA×7.02×dilution factor of enzyme solution.

As the enzyme activity of sarcosine oxidase, the amount of enzyme for producing 1 μmol of hydrogen peroxide in 1 minute in the above reaction condition is defined to be 1 unit (1 U).

PHYSICOCHEMICAL PROPERTIES

1) Enzyme Action

This enzyme has an action to catalyze the reaction to oxidize sarcosine and generating glycine, formaldehyde and hydrogen peroxide.

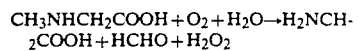

$$CH_3NHCH_2COOH + O_2 + H_2O \rightarrow H_2NCH_2COOH + HCHO + H_2O_2$$

The value of Km (Michaelis constant) to sarcosine is 0.91 mM (37° C., pH 8.0).

2) Optimum pH

As shown in FIG. 1, the optimum pH is around 7.0 to 9.0. The buffers used in measurement were pH 6.0 to 7.5: 0.1M phosphate buffer, pH 7.5 to 9.0: 0.1M tris-HCl buffer, and pH 9.0 to 10.0: 0.1M carbonate buffer.

3) pH Stability

Adding enzyme to buffers at various pH levels, and allowing to stand for 1 hour at 37° C., the residual activity was measured. The buffers used were pH 3.0 to 7.5: 0.1M citrate buffer, pH 7.0 to 9.0: 0.1M tris-HCl buffer, and pH 8.5 to 11.0: 0.1M carbonate buffer. As shown in FIG. 2, its pH stability is near pH 7.0 to 9.0.

4) Thermal Stability

Adding enzyme to 10 mM tris-HCl buffer (pH 8.0) and treating for 10 minute at various temperatures, the residual activity was measured. As shown in FIG. 3, the thermal stability is about 40° C. or less.

5) Molecular Weight

Approx. 44000 (as measured by gel filtration method).

DETAILED DESCRIPTION OF THE INVENTION

Figure 1:
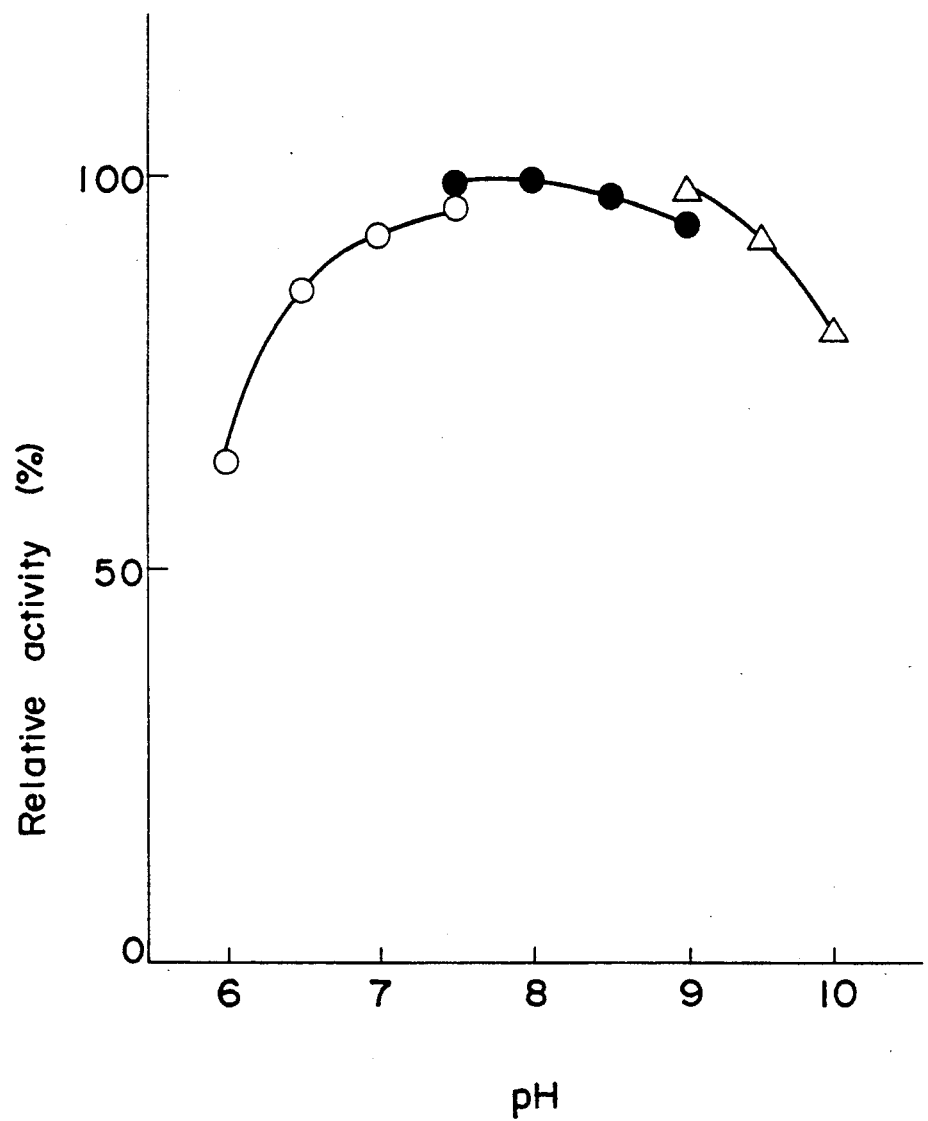
FIG. 1 is a diagram showing the optimum pH range of sarcosine oxidase.
Figure 2:
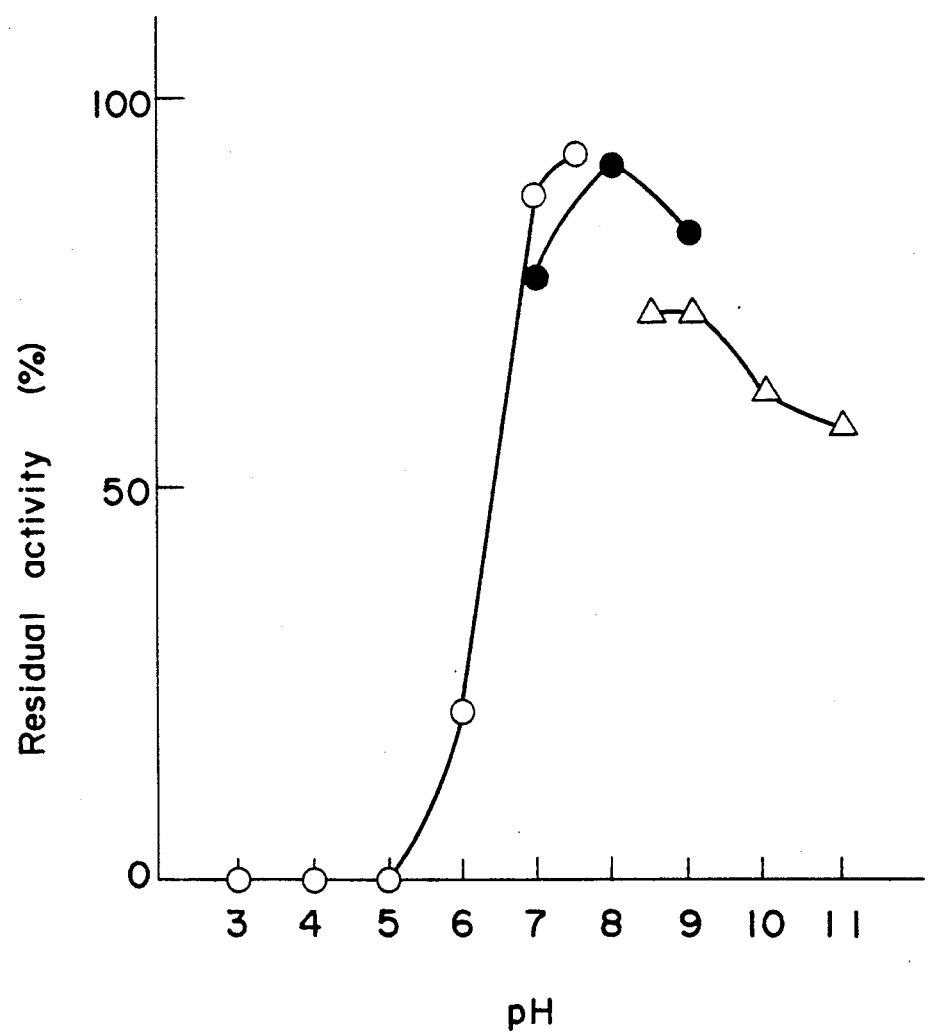
FIG. 2 is a diagram showing the pH stability region of sarcosine oxidase.
Figure 3:
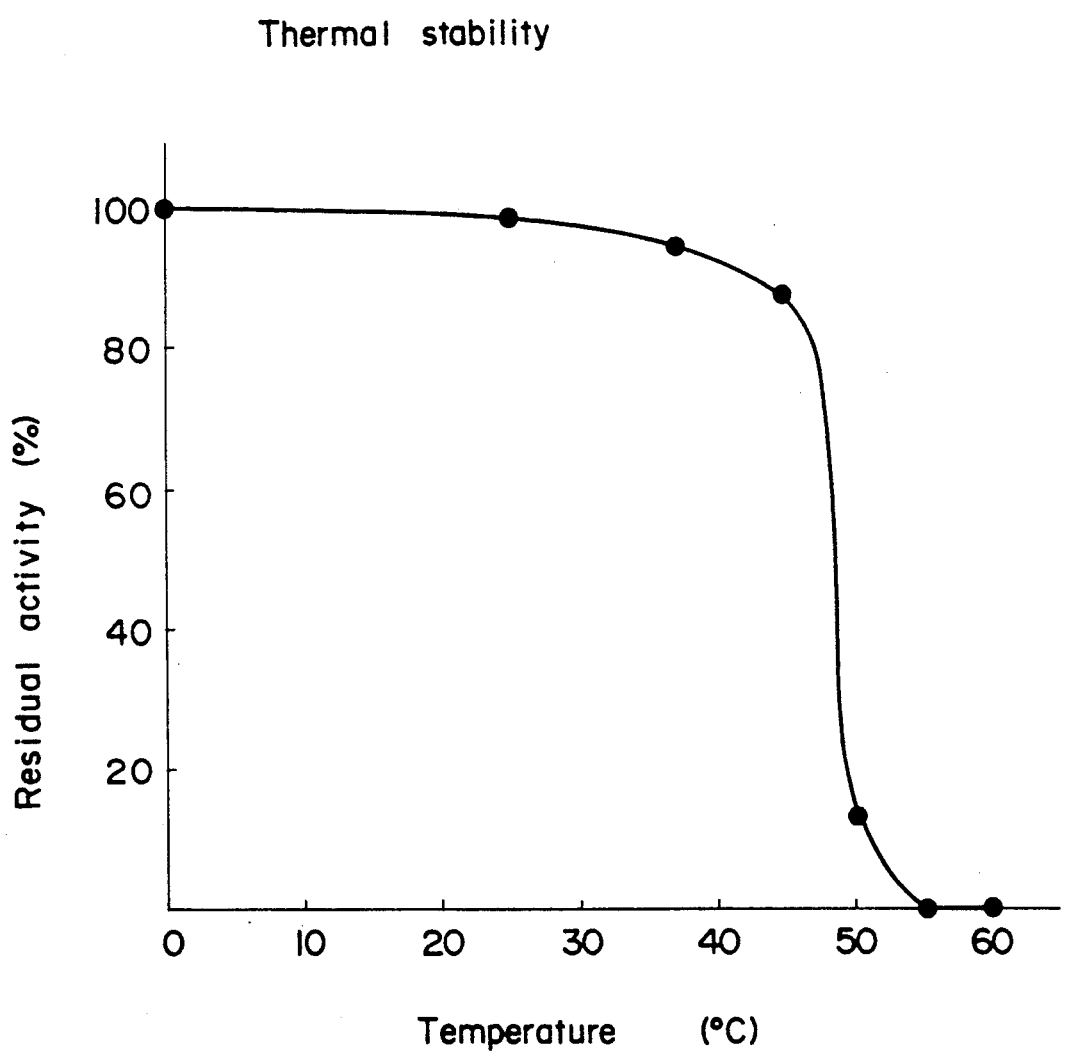
FIG. 3 is a diagram showing the thermal stability range of sarcosine oxidase.

This invention is described in further details below by referring to an example thereof.

Example 1

110 ml of culture medium (pH 7.4) comprising corn steep liquor 2.0% (w/v), soluble starch 1.5% (w/v), glucose 1.5% (w/v), yeast extract 0.3% (w/v), sodium chloride 0.2% (w/v) and calcium carbonate 0.32% (w/v) was put into a 500 ml capacity Sakaguchi flask, and was autoclaved for 20 minutes at 120° C., and Streptomyces sp. KB210-8SY was inoculated and subjected to shake culture for 48 hours at 27° C., and the seed cultures were obtained. The seed cultures were transferred to a 10-liter capacity jar fermenter after sterilization containing 5 liters of culture medium (pH 7.5) comprising corn step liquor 2.0% (w/v) soluble starch 1.5% (w/v), glucose 1.5% (w/v), yeast extract 0.3% (w/v), choline chloride 0.5% (w/v), sodium chloride 0.2% (w/v), and calcium carbonate 0.32% (w/v), and subjected to aeration and agitation culture for 60 hours at 27° C. in the sterilized air condition of 600 rpm, 0.8 liter/minute.

The obtained culture was cooled and centrifuged for 20 minutes at 3500 rpm, and cells and other solid matter were removed, and 4300 ml of broth containing crude sarcosine oxidase (sarcosine oxidase enzyme activity 320 U) was obtained. To this crude enzyme broth, 2044 g of ammonium sulfate was added, and the precipitate was recovered. This precipitate was dissolved in 150 ml of 10mM tris-HCl buffer (pH 8.0), and the same buffer was dialyzed overnight, and 20 ml of this solution was charged into a column (dia. 3 cm by 21 cm) filled with diethylamino ethyl-sepharose (made by Wattman) equilibrated with 10 mM tris-HCl buffer (pH 8.0), and was washed in the same buffer, and then eluted with a linear gradient of 0 to 0.7M of sodium chloride, and the active fractions were recovered. These active fractions were concentrated by using an ultrafiltration unit (made by Toyo Kagaku Sangyo), and was dialyzed overnight in 10 mM tris-HCl buffer (pH 8.0), and this solution was freeze-dried, and powder of sarcosine oxidase was obtained (total activity: 17.5 U, protein: 3.24 mg, specific activity: 5.4 U/mg, recovery: 73%).

Thus, according to this invention, by cultivating the microorganisms belonging to genus Streptomyces and possessing an ability to produce sarcosine oxidase, sarcosine oxidase can be obtained mainly from outside the cells of the obtained culture, and the purifying operation is very simple, and sarcosine oxidase can be obtained easily and efficiently.

A deposit of the streptomyces sp. KB210-8SY culture has been made at the Fermentation Research Institute, Agency of Industrial Science and Technology, 1-3, Higashi 1-chome, Yatabe-machi, Tsukuba-gun, Ibaraki-ken, 305, Japan on Feb. 17, 1987 with a deposit number of FERM BP-1292.

What is claimed is:

1. A process for producing sarcosine oxidase comprising cultivating Streptomyces sp. KB210-8SY, having the ability to produce sarcosine oxidase, in a liquid culture medium by shaking or aerating and agitating, and collecting sarcosine oxidase from the culture medium obtained.

2. A process according to claim 1, wherein said culture medium includes a choline derivative.

* * * * *